United States Patent
Nahama et al.

(10) Patent No.: US 12,029,725 B2
(45) Date of Patent: Jul. 9, 2024

(54) METHOD FOR TREATING OSTEOARTHRITIS PAIN BY ADMINISTERING RESINIFERATOXIN

(71) Applicant: Vivasor, Inc., San Diego, CA (US)

(72) Inventors: Alexis Nahama, San Diego, CA (US); Henry Hongjun Ji, Rancho Santa Fe, CA (US)

(73) Assignee: Vivasor, Inc., San Diego, CA (US)

( * ) Notice: Subject to any disclaimer, the term of this patent is extended or adjusted under 35 U.S.C. 154(b) by 84 days.

(21) Appl. No.: 17/424,634

(22) PCT Filed: Jan. 21, 2020

(86) PCT No.: PCT/US2020/014361
§ 371 (c)(1),
(2) Date: Jul. 21, 2021

(87) PCT Pub. No.: WO2020/154261
PCT Pub. Date: Jul. 30, 2020

(65) Prior Publication Data
US 2022/0096428 A1    Mar. 31, 2022

Related U.S. Application Data

(60) Provisional application No. 62/915,802, filed on Oct. 16, 2019, provisional application No. 62/795,530, filed on Jan. 22, 2019.

(51) Int. Cl.
A61K 31/357     (2006.01)
A61P 19/02      (2006.01)
A61P 29/00      (2006.01)

(52) U.S. Cl.
CPC ............ *A61K 31/357* (2013.01); *A61P 19/02* (2018.01); *A61P 29/00* (2018.01)

(58) Field of Classification Search
CPC ...... A61K 31/357; A61K 47/02; A61K 47/10; A61K 47/26; A61K 9/0019; A61P 19/02; A61P 29/00; C07D 493/18
USPC ........................................................ 514/452
See application file for complete search history.

(56) References Cited

U.S. PATENT DOCUMENTS

| | | |
|---|---|---|
| 7,432,275 B2 | 10/2008 | Bakthavatchalam et al. |
| 8,338,457 B2 | 12/2012 | Iadarola et al. |
| 9,827,223 B2 | 11/2017 | Iadarola et al. |
| 2004/0156931 A1 | 8/2004 | Burch et al. |

(Continued)

FOREIGN PATENT DOCUMENTS

| | | | |
|---|---|---|---|
| CA | 2594202 | * | 7/2006 |
| JP | 5775246 B2 | | 9/2015 |

(Continued)

OTHER PUBLICATIONS

Ladarola et al., Long-term pain relief in canine osteoarthritis by a single intra-articular injection of resiniferatoxin, a potent TRPV1 agonist, Pain (2018), 159(10), 2105-2114) (Year: 2018).*

(Continued)

*Primary Examiner* — Taylor V Oh
(74) *Attorney, Agent, or Firm* — McNeill Baur PLLC

(57) ABSTRACT

Disclosed herein are methods of administering resiniferatoxin (RTX) for treatment of osteoarthritis (OA) pain, and compositions for use in such methods.

18 Claims, 3 Drawing Sheets

(56) References Cited

U.S. PATENT DOCUMENTS

| | | |
|---|---|---|
| 2005/0215575 A1 | 9/2005 | Bakthavatchalam et al. |
| 2007/0036876 A1 | 2/2007 | Burch et al. |
| 2008/0139641 A1 | 6/2008 | Meyer |
| 2010/0222385 A1 | 9/2010 | Iadarola et al. |
| 2015/0190509 A1 | 7/2015 | Giller |
| 2017/0296506 A1 | 10/2017 | Zucker et al. |
| 2021/0393515 A1 | 12/2021 | Nahama |
| 2022/0096428 A1 | 3/2022 | Nahama et al. |
| 2023/0270713 A1 | 8/2023 | Nahama |

FOREIGN PATENT DOCUMENTS

| | | |
|---|---|---|
| WO | 9909970 A1 | 3/1999 |
| WO | 2006069451 A1 | 7/2006 |
| WO | 2008109026 A1 | 9/2008 |
| WO | 2017087803 A1 | 5/2017 |
| WO | 2020132553 A1 | 6/2020 |
| WO | 2020139797 A1 | 7/2020 |
| WO | 2022245791 A1 | 5/2022 |

OTHER PUBLICATIONS

Adrian et al, "Chronic maladaptive pain in cats: A review of current and future drug treatment options", Veterinary Journal, vol. 230, pp. 52-61 (2017).
EP, Extended European Search Report corresponding to European Patent Application No. 19900434.2, dated Aug. 18, 2022, 9 pages.
EP, Extended European Search Report corresponding to European Patent Application No. 20744876.2, dated Oct. 10, 2022, 10 pages.
Kissin et al: "Therapeutic Targeting of TRPVI by Resiniferatoxin, from Preclinical Studies to Clinical Trials", Current Topics in Medicinal Chemistry, vol. 11, No. 17, pp. 2159-2170 (2011).
Kim et al. "The effects of intra-articular resiniferatoxin on monosodium iodoacetate-induced osteoarthritic pain in rats," Korean Journal of Physiology and Pharmacology, 20(1), 129-136 (2016).
Bates, et al. "Prolonged analgesic response of cornea to topical resiniferatoxin, a potent TRPV1 agonist," 149(3):522-528 (2010).
Benito et al. "Feline Musculoskeletal Pain Index: Responsiveness and Testing of Criterion Validity," Journal of Veterinary Internal Medicine, 27: 474-482 (2013).
Brown "Resiniferatoxin: The Evolution of the 'Molecular Scalpel' for Chronic Pain Relief," Pharmaceuticals (Basel), 9(3), pii E47 (2016).
Brown et al. "Intrathecal resiniferatoxin in a dog model: Efficacy in bone cancer pain," Pain, 156(6): 1018-1024 (2015).
Brown et al. "Physiologic and Antinociceptive Effects of Intrathecal Resiniferatoxin in a Canine Bone Cancer Model," Anesthesiology, 103: 1052-1059 (2005).
Currow et al. "Defining refractory pain in cancer for clinicians and researchers," J Palliat Med, 15(1): 5-6 (2012).
Deshpande et al. "Number of Persons With Symptomatic Knee Osteoarthritis in the US: Impact of Race and Ethnicity, Age, Sex, and Obesity," 68(12): 1743-1750 (2016).
Enomoto et al. "Defining the local nerve blocks for feline distal thoracic limb surgery: a cadaveric study," 18(10): 838-845 (2016).
Iadarola et al. "Long-term pain relief in canine osteoarthritis by a single intra-articular injection of resiniferatoxin, a potent TRPV-1 agonist," Pain, 159(10): 2105-2114 (2018).
Iadarola et al. "Resiniferatoxin for pain treatment: an interventional approach to personalized pain medicine," The Open Pain Journal, 6: 95-107 (2013).
Karai et al. "Deletion of vanilloid receptor 1-expressing primary afferent neurons for pain control" Journal of Clinical Investigation, 113(9): 1344-1352 (2004).
Kissin "Vanilloid-Induced Conduction Analgesia: Selective, Dose-Dependent, Long-Lasting, With A Low Level of Potential Neurotoxicity," Anesth. Analg 107(1): 271-281 (2008).
March et al. "Effects of resiniferatoxin on the neurogenic component of feline interstitial cystitis," Urology, (6 Suppl 1):114 (2001).
Martell-Moran NK., Solano M., Townsend HG. Pain and adverse behavior in declawed cats. Journal of Feline Medicine and Surgery, 20(4) 280-288 (2017).
Mourtzoukou et al. "Resiniferatoxin in the treatment of interstitial cystitis: a systematic review," International Urogynecological Journal, 19: 1571-1576 (2008).
Neubert et al. "Perineural resiniferatoxin selectively inhibits inflammatory hyperalgesia," Molecular Pain, 4(3): 1-10 (2008).
Neubert et al. "Peripherally induced resiniferatoxin analgesia" Pain, 104: 219-228 (2003).
Paltser et al. "TRPV1 Gates Tissue Access and Sustains Pathogenicity in Autoimmune Encephalitis," Molecular Medicine, 19: 149-159 (2013).
Patronek GJ. Assessment of claims of short- and long-term complications associated with onychectomy in cats. JAVMA, 219: 932-937 (2001).
PCT, International Search Report and Written Opinion for PCT/US2020/014361 dated May 18, 2020, p. 1-8.
Tender et al. "Selective ablation of nociceptive neurons for elimination of hyperalgesia and neurogenic inflammation," Journal of Neurosurgery, 102(3): 522-525 (2005).
Ueda et al. "Preventive Effect of TRPV1 Agonists Capsaicin and Resiniferatoxin on Ischemia/Reperfusion-induced Renal Injury in Rats," Journal of Cardiovascular Pharmacology, 51(5): 513-520 (2008).
Van Den Beuken-Van Everdingen, et al. "Prevalence of pain in patients with cancer: a systematic review of the past 40 years," Annals of Oncology, 18: 1437-1449 (2007).
Wang et al. "Cardiac Sympathetic Afferent Denervation Attenuates Cardiac Remodeling and Improves Cardiovascular Dysfunction in Rats with Heart Failure" Hypertension, 64(4); 745-755 (2014).
Weintraub "Prickly Painkiller" Scientific America, 309(1): 14-14 (2013).
Yoshie et al. "Cardiac vanilloid receptor-1 afferent depletion enhances stellate ganglion neuronal activity and efferent sympathetic response to cardiac stress," Am J Physiol Heart Circ Physiol, 314(5): H954-H966 (2018).
Gunn-Moore et al., "Oral glucosamine and the management of feline idiopathic cystitis," Journal of Feline Medicine and Surgery, 2004 (6), pp. 219-225.
Bae et al., "Expression of vanilloid receptor TRPV1 in the rat trigeminal sensory nuclei," The Journal of Comparative Neurology 478 (2004) pp. 62-71.
Downie et al., "A quantitative analysis of the afferent and extrinsic efferent innervation of specific regions of the bladder and urethra in the cat," Brain Research Bulletin 12 (1984) pp. 735-740.
Enriquez-Perez et al., "Streptozocin-induced type-1 diabetes mellitus result in decreased density of CGRP sensory and TH sympathetic nerve fibers that are positively correlated with bone loss at the mouse femoral neck," Neuroscience Letters 655 (2017) pp. 28-34.
Farfariello et al., "Resiniferatoxin induces death of bladder cancer cells associated with mitochondrial dysfunction and reduces tumor growth in a xenograft mouse model," Chemico-Biological Interactions vol. 224, pp. 128-135, Oct. 29, 2014 (8 pgs.).
International Search Report and Written Opinion of International Application No. PCT/US2021/038038, dated Sep. 23, 2021, Examiner Giulia Gradassi, 14 pages.
International Search Report and Written Opinion of International Patent Application No. PCT/US2019/0068030, mailed Mar. 13, 2020, Examiner Lee Young, 8 pages.
International Search Report and Written Opinion to International Patent Application No. PCT/US2022/029584, mailed Aug. 3, 2022, Examiner Kari Rodriquez, 8 pages.
Jimenez-Andrade et al., "Capsaicin-sensitive sensory nerve fibers contribute to the generation and maintenance of skeletal fracture pain," Neuroscience 162 (4) (2009), pp. 1244-1254.
Kissin et al., "Memory of Pain: The Effect of Perineural Resiniferatoxin", Anesthesia & Analgesia, vol. 103, Issue 3, pp. 721-728 (2006).
Kraemer et al., "Lumbar epidural perineural injection: a new technique", European Spine Journal, vol. 6, pp. 357-361 (1997).
Peters et al., "Intravenous paclitaxel administration in the rat induces a peripheral sensory neuropathy characterized by macro-

(56) References Cited

OTHER PUBLICATIONS phage infiltration and injury to sensory neurons and their supporting cells," Experimental Neurology 203 (2007) pp. 42-54.

Seki et al., "Intravesical Instillation of Resiniferatoxin for Neurogenic Bladder Dysfunction in A Patient With Myelodysplasia," The Journal of Urology, vol. 166, pp. 2368-2369, Dec. 2001 (2 pages).

Sharrad et al., "Quantitative immunohistochemical co-localization of TRPV1 and CGRP in Varicose axons of the murine oesophagus, stomach and colorectum," Neuroscience Letters 599 (2015) pp. 164-171.

Teater D., "Evidence for the efficacy of pain medications: Saving Jobs, Saving Lives, and Reducing Human Costs," 2014 (8 pages).

\* cited by examiner

METHOD FOR TREATING OSTEOARTHRITIS PAIN BY ADMINISTERING RESINIFERATOXIN

I. CROSS REFERENCE TO RELATED APPLICATIONS

This patent application claims priority to U.S. provisional application 62/795,530 filed Jan. 22, 2019, and U.S. provisional application 62/915,802 filed Oct. 16, 2019, the contents of both of which are incorporated herein by reference in their entirety for all purposes.

II. INTRODUCTION AND SUMMARY

The present disclosure provides methods of treating Osteoarthritis (OA) comprising administering resiniferatoxin, and resiniferatoxin for use in such methods.

Resiniferatoxin (RTX) acts as an ultrapotent analog of capsaicin, the pungent principal ingredient of the red pepper. RTX is a tricyclic diterpene isolated from certain species of *Euphorbia*. A homovanillyl group is an important structural feature of capsaicin and is the most prominent feature distinguishing RTX from typical phorbol-related compounds. Native RTX has the following structure:

RTX and analog compounds such as tinyatoxin and other compounds, (20-homovanillyl esters of diterpenes such as 12-deoxyphorbol 13-phenylacetate 20-homovanillate and mezerein 20-homovanillate) are described in U.S. Pat. Nos. 4,939,194; 5,021,450; and 5,232,684. Other resiniferatoxin-type phorboid vanilloids have also been identified (Szallasi et al. (1999) *Brit. J. Pharmacol.* 128:428-434).

RTX is known as a TrpV1 agonist. TrpV1, the transient receptor potential cation channel subfamily V member 1 (also known as Vanilloid receptor-1 (VR1)) is a multimeric cation channel prominently expressed in nociceptive primary afferent neurons (Caterina et al. (1997) *Nature* 389: 816-824; Tominaga et al. (1998) *Neuron* 21:531-543). Activation of TrpV1 typically occurs at the nerve endings via application of painful heat and is up regulated during certain types of inflammatory stimuli. Activation of TrpV1 in peripheral tissues by a chemical agonist results in the opening of calcium channels and the transduction of a pain sensation (Szalllasi et al. (1999) *Mol. Pharmacol.* 56:581-587). However, direct application of certain TrpV1 agonists to the cell body of a neuron (ganglion) expressing TrpV1 opens calcium channels and triggers a cascade of events leading to programmed cell death ("apoptosis") (Karai et al. (2004) *J. of Clin. Invest.* 113:1344-1352).

Joint pain affects over 30 million patients in major markets, half of which suffer from knee osteoarthritis pain. Osteoarthritis (OA) is a degenerative joint disease that occurs because of the breakdown and erosion of joint cartilage. OA largely affects people 55 years old or greater, nearly one in 12 Americans. The damage to cartilage is associated with inflammation and is progressive. OA is associated with fluid accumulation and structural changes such as bony overgrowth that can restrict movement. OA affects mainly the weight-bearing joints of the knees, hips, and spine, as well as joints in the wrist, fingers, and feet. A nearly universal and dominant symptom is pain, which in later stages can become severe to the point where the patient is a candidate for joint replacement. OA pain is managed by a wide variety of approaches that include lifestyle changes (e.g., weight loss, exercise), topical creams, gels, and patches, systemic drugs including nonsteroidal anti-inflammatory drugs (NSAIDs) and opioids and intraarticular treatments. Nonetheless, OA pain frequently remains an intractable problem in most patients, with many of the commonly prescribed analgesics providing insufficient relief. Joint replacement (e.g., hip or knee) is indicated with severe symptomatic OA. The Centers for Disease Control estimates that over 700,000 total knee replacement (TKR) surgeries are performed per year. While the surgical success rate is high (~90%), the replacement has a finite lifetime, between 15 and 20 years. Revisions are associated with increased complications and expense. Delaying or eliminating the surgery by medically managing the pain can be particularly advantageous in younger patients or in older patients who may not be good surgical candidates.

Intraarticular (IA) injections provide a treatment modality in the continuum of management of OA pain; however, only IA injections of corticosteroids have consistently demonstrated analgesic efficacy. Unfortunately, symptomatic improvement after steroid injections is short (2-4 weeks). The usual recommendation is that the same joint receive no more than 3 injections per year due to concerns for bone deterioration and progressive cartilage damage. Recently, triamcinolone acetonide extended-release injection was approved by the United States Food and Drug Administration (US FDA) as a single injection based on the observed superiority over placebo. However, in a secondary exploratory analysis, statistical significance was not demonstrated between Zilretta and the active control (immediate-release triamcinolone acetonide) so it is unclear what advantage triamcinolone acetonide extended-release injection offers over the immediate release formulation.

Oral agents such as NSAIDs and opioid-containing agents are approved for the treatment of moderate to severe pain. However, these agents have shortcomings with regards to associated adverse effects, including the risk of opioid dependency. These limited options in the therapeutic arsenal for OA highlight the great unmet need for an IA injection agent that provides safe and effective long-term pain relief beyond steroid injections and oral analgesics. Therefore, there is a need in the art for an improved treatment for Osteoarthritis.

Accordingly, the following exemplary embodiments are provided.

Embodiment 1 is a method of treating (OA) pain comprising administering a therapeutically effective amount of resiniferatoxin (RTX) to a subject in need thereof.

Embodiment 2 is a composition comprising resiniferatoxin (RTX) for use in a method of treating osteoarthritis (OA) pain, the method comprising administering a therapeutically effective amount of RTX to a subject in need thereof.

Embodiment 3 is the method or composition for use according to embodiment 1 or 2, wherein the dose of RTX is from about 1 μg to about 100 μg.

Embodiment 4 is the method or composition for use according to embodiment 3 wherein the dose of RTX ranges from 0.1-1 μg, 1-2 μg, 2-5 μg, 5-10 μg, 10-20 μg, 20-30 μg, 30-40 μg, 40-50 μg, 50-60 μg, 60-70 μg, 70-80 μg, 80-90 μg, or 90-100 μg.

Embodiment 5 is the method or composition for use according to embodiment 3, wherein the dose of RTX is from about 5 μg to about 40 μg, from about 10 μg to about 30 μg, from about 15 μg to about 25 μg.

Embodiment 6 is the method or composition for use according to embodiment 3, wherein the dose of RTX is about 12.5 μg.

Embodiment 7 is the method or composition for use according to embodiment 3, wherein the dose of RTX is about 20 μg.

Embodiment 8 is the method or composition for use according to any one of the preceding embodiments, wherein the dose of RTX is about 5 μg, 12.5 μg, 20 μg or 30 μg, optionally wherein the dose is in a volume of about 2.5 ml to about 15 ml, e.g., wherein the volume is about 5 ml or 10 ml.

Embodiment 9 is the method or composition for use according to any one of the preceding embodiments, wherein the administering is by an intra-articular injection to an affected joint.

Embodiment 10 is the method or composition for use according to embodiment 9, wherein the affected joint is a knee joint, a hip joint, a hand joint, a shoulder joint, an ankle joint, a foot joint, an elbow joint, a wrist joint, a sacroiliac joint, or a spine joint, or combinations thereof.

Embodiment 11 is the method or composition for use according to embodiment 9, wherein the affected joint is a large joint.

Embodiment 12 is the method or composition for use according to any one of embodiments 9-11, wherein the RTX is administered to a single site.

Embodiment 13 is the method or composition for use according to any one of embodiments 9-11, wherein the RTX is administered to a plurality of sites.

Embodiment 14 is the method or composition for use according to any one of the preceding embodiments, wherein the method comprises administering a pharmaceutical formulation comprising the RTX and a pharmaceutically acceptable carrier.

Embodiment 15 is the method or composition for use of embodiment 14, wherein the pharmaceutically acceptable carrier comprises water.

Embodiment 16 is the method or composition for use of embodiment 14 or 15, wherein the pharmaceutically acceptable carrier comprises polysorbate 80.

Embodiment 17 is the method or composition for use of any one of embodiments 14-16, wherein the pharmaceutically acceptable carrier comprises polyethylene glycol.

Embodiment 18 is the method or composition for use of any one of embodiments 14-17, wherein the pharmaceutically acceptable carrier comprises a sugar or sugar alcohol.

Embodiment 19 is the method or composition for use of embodiment 18, wherein the pharmaceutically acceptable carrier comprises mannitol.

Embodiment 20 is the method or composition for use of embodiment 18 or 19, wherein the pharmaceutically acceptable carrier comprises dextrose.

Embodiment 21 is the method or composition for use of any one of embodiments 14-20, wherein the pharmaceutically acceptable carrier comprises a pharmaceutically acceptable buffer.

Embodiment 22 is the method or composition for use of embodiment 21, wherein the pharmaceutically acceptable carrier comprises a phosphate buffer.

Embodiment 23 is the method or composition for use of any one of embodiments 14-22, wherein the pharmaceutical formulation has a pH in the range of 6 to 7.6.

Embodiment 24 is the method or composition for use of embodiment 23, wherein the pharmaceutical formulation has a pH in the range of 6 to 6.4, 6.3 to 6.7, 6.4 to 6.8, 6.8 to 7.2, 7 to 7.4, or 7.2 to 7.6.

Embodiment 25 is the method or composition for use of embodiment 23, wherein the pharmaceutical formulation has a pH of 6.5 or 7.2.

Embodiment 26 is the method or composition for use of any one of embodiments 14-25, wherein the pharmaceutically acceptable carrier comprises a pharmaceutically acceptable salt.

Embodiment 27 is the method or composition for use of embodiment 26, wherein the pharmaceutically acceptable salt is NaCl.

Embodiment 28 is the method or composition for use of any one of embodiments 14-27, wherein the concentration of RTX in the pharmaceutical formulation is in the range of 0.1 to 300 μg/ml.

Embodiment 29 is the method or composition for use of embodiment 28, wherein the concentration of RTX in the pharmaceutical formulation is in the range of 0.1-1 μg/ml, 1-5 μg/ml, 5-10 μg/ml, 10-20 μg/ml, 20-50 μg/ml, 50-100 μg/ml, 100-150 μg/ml, 150-200 μg/ml, 200-250 μg/ml, or 250-300 μg/ml.

Embodiment 30 is the method or composition for use of embodiment 28 or 29, wherein the concentration of RTX in the pharmaceutical formulation is in the range of 150 to 250 μg/ml, or 200 μg/ml.

Embodiment 31 is the method or composition for use of any one of the preceding embodiments, wherein the subject is a mammal.

Embodiment 32 is the method or composition for use of embodiment 31, wherein the subject is a cat, dog, horse, pig, ruminant, cow, sheep, goat, or domesticated mammal.

Embodiment 33 is the method or composition for use of embodiment 31, wherein the subject is a human.

Embodiment 34 is the method or composition for use of any one of the preceding embodiments, wherein RTX is periodically administered.

Embodiment 35 is the method or composition for use of embodiment 34, wherein RTX is periodically administered about 1, 2, 3, 4, 5, 6, 7, 8, 9, 10, 11, or 12 times per year; 1, 2, or 3 times per month; or 1 or 2 times per week.

Embodiment 36 is the method or composition for use of embodiment 34, wherein the duration of the periodic administration is from about 1 week to about 12 months or more, about 1 week to about 6 months, about 1 month to 4 months, or about 3 months.

Embodiment 37 is the method or composition for use of any one of embodiments 34-36, wherein the duration of the periodic administration is at least 2 weeks, optionally wherein the duration of the periodic administration is at least one month, further optionally wherein the duration of the periodic administration is at least two months.

Embodiment 38 is the method or composition for use of any one of embodiments 34-36, wherein the duration of the periodic administration is at least three months, optionally wherein the duration of the periodic administration is at least four months, further optionally wherein the duration of the periodic administration is at least six months.

III. BRIEF DESCRIPTION OF THE FIGURES

IV. DETAILED DESCRIPTION

Figure 1:
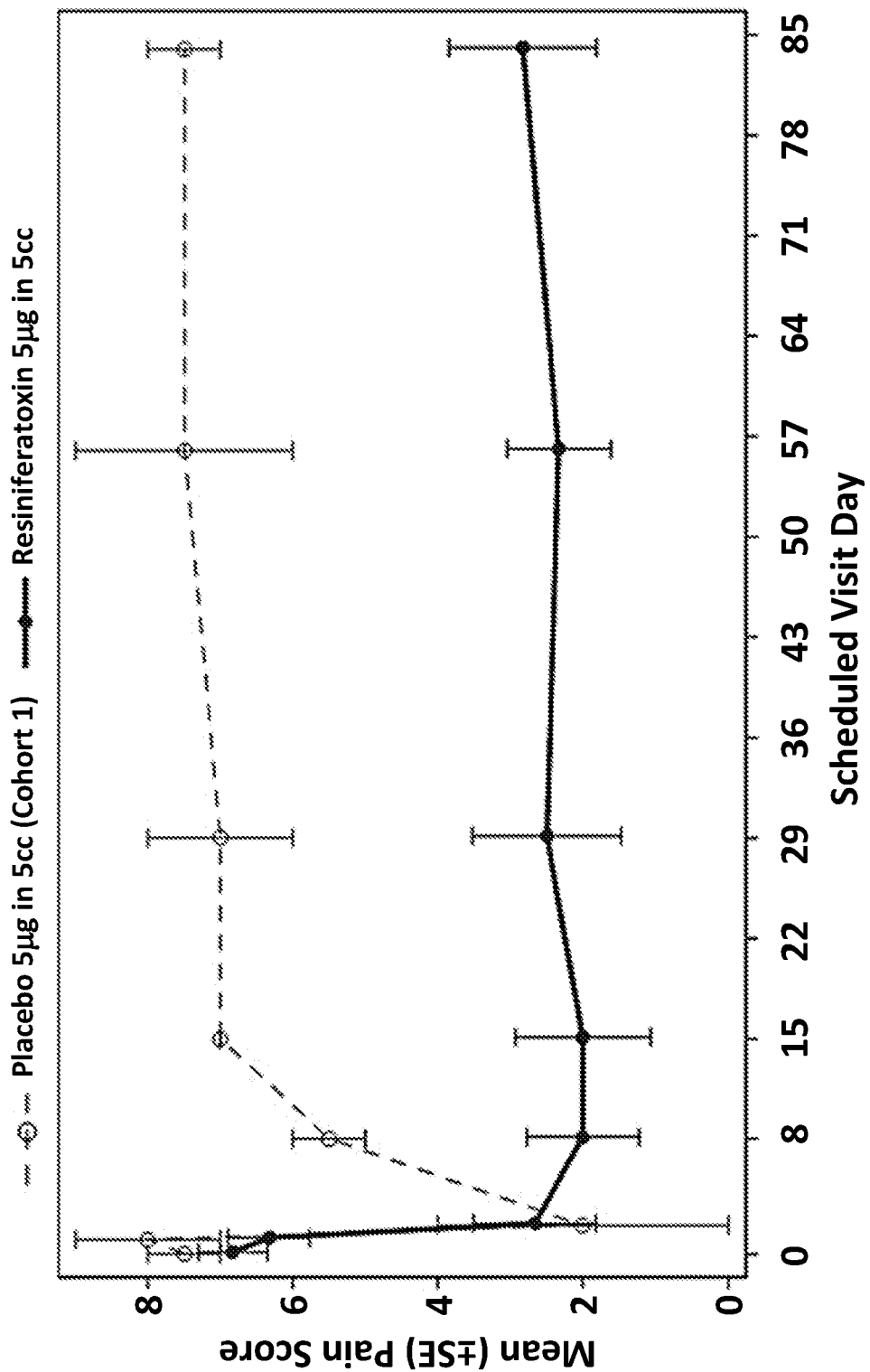
FIG. 1 shows the data from Example 1 demonstrating large pain score differences between RTX treated patients and placebo control patients.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a conjugate" includes a plurality of conjugates and reference to "a cell" includes a plurality of cells and the like.

Numeric ranges are inclusive of the numbers defining the range. Measured and measurable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The section headings used herein are for organizational purposes only and are not to be construed as limiting the desired subject matter in any way. In the event that any literature incorporated by reference contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

A. Definitions

"Osteoarthritis pain" (or "OA pain") refers to the pain caused by osteoarthritis (OA) in a joint of a mammal. The pain is perceived by the mammal to emanate from the affected joint and the tissues surrounding the joint.

"Affected joint" refers to a bone joint in a mammal (a human or non-human mammal) having osteoarthritis and can include any bone joint in the body where cartilage is present. Non-limiting examples of an affected joint include the shoulder joints, the spine, the joints in a hand, the joints in a foot, including the ankle, and the large weight-bearing joints, such as a knee or a hip or spine.

As used herein, a "large joint" refers to a knee, ankle, shoulder, hip or elbow for a human (e.g., an adolescent human, such as a human of 10 or more years of age, or an adult human, such as a human of 18 or more years of age) and equivalent joints in other mammals (e.g., mammals weighing 25 kg or more).

"Intraarticular injection" (or "IA injection" or "intraarticular administration") as used herein is injection of compounds in an aqueous solution into an affected joint, such as a large joint, e.g., the knee or elbow. For example, the volume for intraarticular administration for a human adult knee may be from 3 to 10 ml of volume and 5 to 50 μg of RTX. Knees of pediatric humans or veterinary subjects (such as dog or cats) are lower and proportionate in volume to the relative sizes of each species knees.

"Periodical administration" or "periodically administered" as used herein refers to administration at a plurality of time points including an initial administration of a composition followed by a pre-determined time period and then one or more further administrations, each of which may also be separated by about the same pre-determined time period. The pre-determined time period can be, e.g., from about 4 hours to about 24 hours.

The terms "or a combination thereof" and "or combinations thereof" as used herein refers to any and all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

"Or" is used in the inclusive sense, i.e., equivalent to "and/or," unless the context requires otherwise.

B. Methods and Compositions for Use

Provided herein are methods for treating osteoarthritis (OA) pain comprising administering a therapeutically effective amount of resiniferatoxin (RTX) to a subject in need thereof. Also provided are compositions comprising resiniferatoxin (RTX) for use in a method of treating OA pain, the method comprising administering a therapeutically effective amount of RTX to a subject in need of treatment of OA pain.

Without wishing to be bound by any particular theory, administration of RTX to treat osteoarthritis pain by intraarticular injection as disclosed herein may provide benefits, such as allowing safe and effective long-term pain relief beyond steroid injections and oral analgesics such as NSAIDs and opioid-containing agents that have shortcomings with regards to associated adverse effects, including the risk of various NSAID side effects (e.g., stomach pain, stomach ulcers, increased bleeding/reduced blood clotting, etc.) and opioid dependency, respectively.

1. Subjects

The compositions and methods described herein are for use with any subject in whom RTX is effective, e.g., able to bind and activate TrpV1 or a homolog thereof, and who is in need of treatment for osteoarthritis pain. In some embodiments, the subject is a mammal. In some embodiments, the mammal is a human. In some embodiments, the mammal is a cat. In some embodiments, the mammal is a dog. In some embodiments, the mammal is a ruminant. In some embodiments, the mammal is a horse, cow, pig, sheep, or goat.

In some embodiments, the subject suffers from osteoarthritis pain. For example, the osteoarthritis pain may occur at any bone joint in the body where cartilage is present. Non-limiting examples of an affected joint include the shoulder joints, the spine, the joints in a hand, the joints in a foot, including the ankle, and the large weight-bearing joints, such as a knee or a hip or spine.

In some embodiments, the subject had one or more symptoms of osteoarthritis prior to treatment and the treatment reduces or eliminates the one or more symptoms. For example, symptoms osteoarthritis include stiffness, joint swelling, decreased range of motion, and, when the back is affected, weakness or numbness of the arms and legs.

2. Sites of Administration

In some embodiments, the RTX is administered by intraarticular injection. Injections may be performed, e.g., using a size of syringe appropriate for the dosage volume, which may be a 1 cc syringe.

RTX may be administered by intraarticular injection to one or more than one site, depending on the joints responsible for the osteoarthritis pain. In some embodiments, the RTX is administered by intraarticular injection to a single site. In some embodiments, the RTX is administered by intraarticular injection to a plurality of sites.

In some embodiments, the RTX is administered to a knee joint. In some embodiments, the RTX is administered to a hip joint. In some embodiments, the RTX is administered to a hand joint. In some embodiments, the RTX is administered to a shoulder joint. In some embodiments, the RTX is administered to an ankle joint. In some embodiments, the RTX is administered to a foot joint. In some embodiments, the RTX is administered to an elbow joint. In some embodiments, the RTX is administered to a wrist joint. In some embodiments, the RTX is administered to a sacroiliac joint. In some embodiments, the RTX is administered to a spine joint.

3. Dosage

In some embodiments, the RTX is administered at a dose of 0.1-100 µg. In some embodiments, the dose of RTX ranges from 0.1-0.5 µg, 0.5-1 µg, 1-2 µg, 2-5 µg, 5-10 µg, 10-20 µg, 20-30 µg, 30-40 µg, 40-50 µg, 50-60 µg, 60-70 µg, 70-80 µg, 80-90 µg, or 90-100 µg.

The dosage and volume can be adjusted depending on the proximity of the site of administration to the affected joint as well as the size of the joint. Notably, RTX is specific for the TRPV1 receptor and therefore does not affect non-target nerves, such as motor neurons, that do not have enough TRPV1 receptors to be sensitive to RTX.

The dosage and volume can be adjusted depending on the size of the affected joint. For a large joint of an adult human, a higher dose and volume can be used.

The foregoing doses are administered intraarticularly in volumes of 2.5-15 ml depending on the joint and the size of the individual subject. In some embodiments, the RTX is administered at 5 µg in 2.5-15 ml. In some embodiments, the RTX is administered at 12.5 µg in 2.5-15 ml. In some embodiments, the RTX is administered at 20 µg in 2.5-15 ml. In some embodiments, the RTX is administered at 12.5 µg in 2.5 ml. In some embodiments, the RTX is administered at 12.5 µg in 5 ml. In some embodiments, the RTX is administered at 12.5 µg in 10 ml. In some embodiments, the RTX is administered at 12.5 µg in 15 ml. In some embodiments, the RTX is administered at 20 µg in 2.5 ml. In some embodiments, the RTX is administered at 20 µg in 5 ml. In some embodiments, the RTX is administered at 20 µg in 10 ml. In some embodiments, the RTX is administered at 20 µg in 15 ml.

The concentration of intraarticular injection of the RTX is adjusted according to dose of RTX and volume to be injected to achieve the selected dose of RTX to be administered. In some embodiments, the dose of RTX is from about 1 µg/ml to about 100 µg/ml. In some embodiments, the dose of RTX is from about 5 µg/ml to about 40 µg/ml. In some embodiments, the dose of RTX is about 20 µg/ml.

In some embodiments, RTX may be administered as a one-time single dose. In some embodiments, RTX is periodically administered. In some embodiments, RTX is periodically administered to a subject in need of treatment for osteoarthritis pain by intraarticular injection to an affected joint as needed to reduce the severity of the pain and/or to alleviate the pain. In some embodiments, RTX is administered once a day (e.g., about every 24 hours). In some embodiments, RTX is administered 1-12 times per year, 1-3 times per month, or 1-2 times per week. The specified duration of time for the periodic administration is intended to be as long as needed to alleviate or substantially relieve the pain and/or to alleviate and maintain relief of the pain. In some embodiments, the duration of the periodic administration is from about 1 week to about 12 months or more, 1 week to about 6 months, from about 1 month to 4 months, about 1 month to 2 months, about 2 to 3 months, or about 3 to 4 months (e.g., about 2 months, or about 3 months). In some embodiments, the duration of periodic administration is at least 2 weeks, at least one month, at least 2 months, at least 3 months, at least 4 months, or at least 6 months.

4. Formulations

Multiple examples of formulations of RTX are available in the literature. See, e.g., Ueda et al. (2008) *J. of Cardiovasc. Pharmacol.* 51:513-520, and US 2015/0190509 A1. Any suitable formulation of RTX for parenteral administration (e.g., injection) may be used.

In some embodiments, RTX, which may be at the dosages discussed above, is administered with a pharmaceutically acceptable carrier. In some embodiments, the pharmaceutically acceptable carrier comprises water. In some embodiments, the pharmaceutically acceptable carrier comprises polysorbate 80. In some embodiments, the pharmaceutically acceptable carrier comprises polyethylene glycol. In some embodiments, the pharmaceutically acceptable carrier comprises sugar or sugar alcohol. In some embodiments, the pharmaceutically acceptable carrier comprises mannitol. In some embodiments, the pharmaceutically acceptable carrier comprises dextrose. In some embodiments, the pharmaceutically acceptable carrier comprises a pharmaceutically acceptable buffer. In some embodiments, the pharmaceutically acceptable carrier comprises a phosphate buffer. In some embodiments, the pharmaceutically acceptable carrier comprises a pharmaceutically acceptable salt. In some embodiments, the pharmaceutically acceptable carrier comprises NaCl. In some embodiments, the pharmaceutically acceptable carrier comprises an organic solvent such as ethanol or DMSO, e.g., as a minority or residual component used as an aid in dissolving RTX before dilution in a primarily aqueous composition. In other embodiments, RTX is prepared in a formulation comprising a combination of two or more pharmaceutically acceptable carriers, which may include any of the foregoing pharmaceutically acceptable carriers.

The concentration of RTX in the formulation may be any suitable value for delivery of the intended dose. In some embodiments, the concentration of RTX in the pharmaceutical formulation is in the range of 0.1 to 300 µg/ml. In some embodiments, the concentration of RTX in the pharmaceutical formulation is in the range of 0.1-1 µg/ml, 1-5 µg/ml, 5-10 µg/ml, 10-20 µg/ml, 10-30 µg/ml, 20-30 µg/ml, 20-50 µg/ml, 50-100 µg/ml, 100-150 µg/ml, 150-200 µg/ml, 200-250 µg/ml, or 250-300 µg/ml. In some embodiments, the concentration of RTX in the pharmaceutical formulation is in the range of 150 to 250 µg/ml, or 200 µg/ml.

The formulation may have any pH suitable for intra-articular administration. In some embodiments, the pharmaceutical formulation comprising RTX and a pharmaceutically acceptable carrier has a pH in the range of 6 to 7.6. In some embodiments, the pharmaceutical formulation comprising RTX and a pharmaceutically acceptable carrier has a pH in the range of 6 to 6.4, 6.3 to 6.7, 6.4 to 6.8, 6.8 to 7.2, 7 to 7.4, or 7.2 to 7.6. In some embodiments, the pharmaceutical formulation comprising RTX and a pharmaceutically acceptable carrier has a pH of 6.5 or 7.2.

In some embodiments, the formulation comprises polysorbate 80 and dextrose. In some embodiments, the concentration of polysorbate 80 is 2-4% w/v, and/or the concentration of dextrose is 4-6% w/v. In some embodiments, the concentration of polysorbate 80 is 3% w/v, and/or the concentration of dextrose is 5% w/v. In some embodiments, in any of the foregoing formulations, the concentration of RTX may be 10-30 µg/ml, such as 10 µg/ml or 25 µg/ml. In some embodiments, the formulation further comprises phosphate buffer, e.g., at a concentration and pH shown for phosphate buffer in Table 1. In some embodiments, the formulation further comprises NaCl, e.g., at a concentration shown for NaCl in Table 1. When both are present, the phosphate buffer and NaCl may be (but are not necessarily) present at a combination of concentrations and phosphate buffer pH shown for an individual formulation.

Exemplary formulations of RTX are shown in the following table.

TABLE 1

Exemplary RTX Solution Formulations

| Formulation Number | Formulation Components | Component Concentration |
|---|---|---|
| 1 | RTX | 200 µg/mL |
|   | Polysorbate 80 | 7.0% w/v |
|   | Dextrose | 0.8% w/v |
|   | 30 mM Phosphate Buffer w/0.44% NaCl | 30 mM, pH 7.2 |
| 2 | RTX | 200 µg/mL |
|   | Polyethylene Glycol 300 | 3.0% v/v |
|   | Polysorbate 80 | 0.1% w/v |
|   | Dextrose | 0.8% w/v |
|   | 10 mM Phosphate Buffer w/0.73% NaCl | 10 mM, pH 6.5 |
| 3 | RTX | 200 µg/mL |
|   | Polyethylene Glycol 300 | 30.0% v/v |
|   | Polysorbate 80 | 1.0% w/v |
|   | 10 mM Phosphate Buffer w/0.86% NaCl | 10 mM, pH 6.5 |
| 4 | RTX | 200 µg/mL |
|   | Polyethylene Glycol 300 | 30.0% v/v |
|   | Polysorbate 80 | 0.04% w/v |
|   | 10 mM Phosphate Buffer w/0.88% NaCl | 10 mM, pH 6.5 |
| 5 | RTX | 200 µg/mL |
|   | Polysorbate 80 | 3.0% w/v |
|   | Dextrose | 0.8% w/v |
|   | 30 mM Phosphate Buffer w/0.54% NaCl | 30 mM, pH 7.2 |
| 6 | RTX | 200 µg/mL |
|   | Polysorbate 80 | 3.0% w/v |
|   | Mannitol | 0.8% w/v |
|   | 30 mM Phosphate Buffer w/0.54% NaCl | 30 mM, pH 7.2 |
| 7 | RTX | 200 µg/mL |
|   | Polysorbate 80 | 7.0% w/v |
|   | Mannitol | 0.8% w/v |
|   | 30 mM Phosphate Buffer w/0.45% NaCl | 30 mM, pH 7.2 |
| 8 | RTX | 200 µg/mL |
|   | Polyethylene Glycol 300 | 3.0% v/v |
|   | Polysorbate 80 | 0.1% w/v |
|   | Mannitol | 0.8% w/v |
|   | 10 mM Phosphate Buffer w/0.74% NaCl | 10 mM, pH 6.5 |
| 9 | RTX | 200 µg/mL |
|   | Polyethylene Glycol 300 | 3.0% v/v |
|   | Polysorbate 80 | 0.1% w/v |
|   | Dextrose | 3.0% w/v |
|   | 10 mM Phosphate Buffer w/0.34% NaCl | 10 mM, pH 6.5 |

TABLE 1-continued

Exemplary RTX Solution Formulations

| Formulation Number | Formulation Components | Component Concentration |
|---|---|---|
| 10 | RTX | 200 µg/mL |
|  | Polyethylene Glycol 300 | 3.0% v/v |
|  | Polysorbate 80 | 0.1% w/v |
|  | Mannitol | 3.0% w/v |
|  | 10 mM Phosphate Buffer w/0.36% NaCl | 10 mM, pH 6.5 |
| 11 | RTX | 200 µg/mL |
|  | Polysorbate 80 | 0.03% w/v |
|  | Dextrose | 0.05% w/v |
|  | 30 mM Phosphate Buffer w/0.54% NaCl | 30 mM, pH 7.2 |

In some embodiments, the concentration of RTX in a formulation shown in Table 1 is adjusted to any of the RTX concentrations or concentration ranges disclosed herein. For example, in some embodiments, the concentration of RTX in a formulation shown in Table 1 is adjusted to a value in the range of 10-50 µg/ml. As another example, in some embodiments, the concentration of RTX in a formulation shown in Table 1 is adjusted to a value in the range of 10-30 µg/ml. As another example, in some embodiments, the concentration of RTX in a formulation shown in Table 1 is adjusted to a value in the range of 20-30 µg/ml. As another example, in some embodiments, the concentration of RTX in a formulation shown in Table 1 is adjusted to 25 µg/ml.

The formulations in Table 1 may be prepared according to the following exemplary methods, which are provided for formulations 3 and 5 but may be adapted to the other formulations by one skilled in the art. Formulation 3 may be made by preparing a 30 mM, pH 7.2 phosphate buffer. Then 1.43% w/v polysorbate 80 and 0.86% w/v NaCl are mixed to form the aqueous component. 20 mg of RTX is added to 100 mL of the aqueous component in a volumetric flask. Then 30 mL of PEG 300 is added and the solution is sonicated to dissolve the solids. The aqueous component is added to about 80% volume, and then it is sonicated to mix. It should be noted that RTX will sometimes precipitate at the interface of aqueous solution and PEG initially, but will go back into solution upon sonication. The full mixture in the flask is diluted to volume with the aqueous component and this is mixed by an inversion process. The full formulation is filtered through a 0.2 µm polytetrafluoroethylene (PTFE) filter.

Formulation 5 may be made by preparing 30 mM, pH 7.2 phosphate buffer. Then 3.0% w/v polysorbate 80, 0.8% w/v dextrose, and 0.54% w/v NaCl are mixed together to form the aqueous component. 20 mg of RTX is added to 100 mL of the aqueous component in a volumetric flask. The aqueous component is added to about 80% volume, and then it is sonicated to dissolve all the solids. (Alternatively, the RTX may be initially dissolved in a small volume of ethanol or DMSO, and this solution may then be added to the aqueous component.) The full mixture in the flask is diluted to volume with the aqueous component and this is mixed by an inversion process. The full formulation is filtered through a 0.2 µm PTFE filter.

A formulation according to Formulation 11 is prepared using 200 µg RTX, 20 mg Polysorbate 80 (using commercially-available polysorbate 80); 5.4 mg of sodium chloride, 50 mg of dextrose, and a 30 mM aqueous phosphate buffer, water (WFI) to 1 mL.

In some embodiments, the pharmaceutical formulation is in a unit dosage form. In such form, the preparation is subdivided into unit doses containing appropriate quantities of the active component. The unit dosage form can be a packaged preparation, the package containing discrete quantities of formulation, such as in vials, ampoules, or pre-loaded syringes. Also, the unit dosage form can be, e.g., a solution or a lyophilized composition for reconstitution.

Further details on techniques for formulation and administration may be found in Gennaro, A., Ed., Remington's Pharmaceutical Sciences, 18th Ed. (1990) (Mack Publishing Co., Easton, Pa.).

V. EXAMPLES

Example 1—Methods

The study, described as "Phase 1b double-blind study assesses safety and preliminary efficacy of intra-articular administration of resiniferatoxin versus placebo for the treatment of pain due to moderate to severe osteoarthritis of the knee," was performed.

Subjects with moderate to severe osteoarthritis diagnosed based on ACR diagnostic criteria and X-ray imaging were enrolled in a phase 1b double-blind study to assess the safety, tolerability and preliminary efficacy of intra-articular administration of resiniferatoxin or placebo for the treatment of moderate to severe pain due to osteoarthritis of the knee. Patients met the following criteria: (1) baseline pain score in the index knee (WOMAC pain subscale question A1) of ≥5 but ≤9 during four weeks prior to enrollment; (2) mean NPRS score of ≥5 but ≤9 during 8 of 10 days prior to enrollment; and (3) pain lasted for at least 6 months prior to enrollment.

As of August 2019, the enrollment of all planned dose level cohorts was completed. 40 patients have enrolled in these dose-escalation cohorts, 30 receiving RTX and 10 receiving placebo (multicenter, randomized, double-blind, placebo controls). In each cohort, six patients received intraarticular RTX and two received a saline control (placebo arm). The demographic information of the patients is shown in Table 2. 69% are female and 31% are male. The median age is 62 (range 44-83), and the baseline NPRS A1 score was mean 6.5 (S.D. 1.5).

The patients were treated with a one-time intraarticular dose of resiniferatoxin (RTX) or saline placebo at escalating dose level cohorts of 5 µg, 12.5 µg, 20 µg and 30 µg in 5 or 10 mL in dose escalation cohorts. For each 8-patient cohort, the first patient was considered a sentinel patient and received open-label drug. Upon confirmation of safety in the sentinel patient, the remaining 7 patients in the cohort were enrolled in a blinded fashion, 2 patients receiving placebo and 5 patients receiving RTX. After confirmation of safety at each dose level, the next higher dose level was opened for enrollment. Patients were followed for safety and efficacy over a 12-week period. Patients had the option to provide additional follow-up to 52 weeks. Efficacy was assessed using the patient reported WOMAC pain scores and NPRS pain scores. As per protocol, the treatment assignment could be unblinded at week 12.

TABLE 2

Demographic information of the patients and placebo treated

| Baseline characteristics | Placebo, Pooled; N = 10 | RTX, Pooled Dose Level; N = 30 |
|---|---|---|
| Female, Male | 8 (80%), 2 (20%) | 20 (66.7%), 10 (33.3%) |
| Age, Median (min, mix) | 59.9 (45.1, 78.1) | 62.2 (44.4, 83.6) |
| BMI, Mean (SD) | 33.1 (5.1) | 30.6 (5.9) |
| Kellgren-Lawrence by Investigator | G2: 4 (40%); G3: 6 (60%) | G2: 9 (30%); G3: 21 (70%) |
| # Knees affected by OA | 1 knee: 4 (40%); 2 knees (6 (60%) | 1 knee: 10 (33.3%); 2 knees (20 (66.7%) |
| WOMAC A1, Mean (SD) | 6 (2) | 6 (1) |
| NPRS, Mean (SD) | 6.5 (1.5) | 6.4 (1.4) |

Example 2

This example provides results from an ongoing clinical trial with dose escalation of RTX as described in Example 1.

The initial results of the study found (1) Rapid onset of pain relief (day following injection) and sustained clinical benefits (determined at 84 days) at the lowest dose tested; (2) Pain at walking (10 points WOMAC (Western Ontario and McMaster Universities Osteoarthritis Index) scale) reduced by 4.7 points versus control at day 84; and (3) No dose limiting toxicities (DLTs), nor adverse events of interest noted for any dose group.

The results are summarized in Table 3:

TABLE 3

| Cohort (escalation) | RTX Dose | # Subjects | Status | Blinding status | DMC assessment | Notable AE's |
|---|---|---|---|---|---|---|
| 1 | 5 µg | 6 + 2 | Enrolled | Unblinded | No DLTs | None |
| 2 | 12.5 µg | 6 + 2 | Enrolled | Unblinded | No DLTs | None |
| 3 | 12.5 µg (in 10 ml) | 6 + 2 | Enrolled | Unblinded | No DLTs | None |
| 4 | 20 µg | 6 + 2 | Enrolled | Unblinded | No DLTs | None |
| 5 | 30 µg | 6 + 2 | Enrolled | Unblinded | No DLTs | None |

No dose limiting toxicities have been observed to date at any dose group (see table 3) and a majority of the patients treated with the active drug were reporting positive clinical benefits in pain reduction.

Subjects in the lowest dose cohort were treated with a single injection into the knee joint (with 5 µg RTX) and the cohort was unblinded after twelve weeks of observation as authorized per protocol. The RTX treated patients had a mean pain score 4.7 points lower than controls (on the 10 point WOMAC pain scale) at Day 84 (see FIG. 1). Onset of pain reduction was as early as the day following drug administration and was sustained over time. Patients in all dose groups are also displaying rapid and sustainable improvements. Therefore, these data are able to determine a safe and efficacious dose of RTX.

Results from dose escalation cohorts (N=40) were further analyzed.

No dose-limiting toxicities were reported, and maximum tolerated dose was not identified (i.e., the highest dose administered, 30 ng, was tolerated). The most frequently reported treatment-emergent adverse events were procedure-associated pain (post-procedural pain and injection site pain), which was reported in 62% of placebo patients (pooled) and in 100% of RTX patients. This procedure-associated pain was reported as mild in severity in all placebo patients, while in RTX treated patients the pain was reported as mild in 55% and moderate in 45%. The procedure-associated pain in the RTX treated patients typically lasted 2-3 hrs after RTX injection and was managed with fentanyl and other analgesics. Other less frequently reported adverse events (reported in at least 2 subjects) were nausea, vomiting, hypertension, arthralgia, and headache. All patients could be discharged to home on the day of injection. There was no apparent relationship between adverse events and dose. One SAE of fibula and tibia fracture was considered unrelated.

In terms of efficacy based on available unblinded data, reduction in patient reported WOMAC A1 and NPRS pain scores was observed at all dose levels. The difference in the mean pain score for WOMAC question A1 (pain on walking on flat surface) at week 12 between the pooled placebo patients and RTX treated patients unblinded at the time of this analysis (9 placebo, 28 RTX), expressed as the least squares mean difference in change from baseline relative to placebo, ranged from −0.38 to −2.70 points depending on the dose level cohort. When analyzed as the change in the weekly average NPRS pain score from baseline to week 12, the difference between the pooled placebo patients and RTX treated patients ranged from −0.34 to −2.29, depending on the dose level cohort. Compared to baseline pain, >70% reduction in the pain was achieved in 54% of pooled RTX-treated patients based on the WOMAC A1 score and in 41% of patients based on the NPRS score. By mixed model repeated measures (MMRM) analysis, the greatest pain reduction was observed at the 12.5 µg dose (least squares mean difference versus placebo at 12 weeks of −2.29 by NPRS score (p=0.051, N=6); −2.70 by WOMAC A1 score (p=0.029, N=6); and −14.20 by WOMAC A-C pain index (p=0.016, N=6)).

Thus, resiniferatoxin demonstrated safety and preliminary efficacy when given as one-time intra-articular injection up to the planned highest dose of 30 µg.

Results from all cohorts were further analyzed. In addition to dose escalation cohorts, 1 cohort at different volume and additional 4 cohorts of dose expansion (testing two administration of analgesics to control pain of procedure) were included.

No dose-limiting toxicities were reported, and a maximum tolerated dose was not identified. The most frequently reported treatment-emergent adverse events were procedure-associated pain (post-procedural pain and injection site pain), which was reported in 70% of placebo patients (pooled) and in 91% of RTX patients. This procedure-associated pain was reported as mild in severity in all placebo patients, while in RTX treated patients the pain was reported as mild in 65% and moderate in 26%. The procedure-associated pain in the RTX treated patients typically lasted 2-3 hours after RTX injection and was managed with fentanyl and other analgesics. Other less frequently reported adverse events (reported in at least 2 subjects) were nausea, vomiting, hypertension, arthralgia, hypoaesthesia, areflexia, EOG QTc prolonged, and headache as detailed in Table 4. All patients could be discharged to home on the day of injection. There was no apparent relationship between adverse events and dose. One SAE of fibula and tibia fracture was considered unrelated.

Table 4 shows frequency of treatment-emergent adverse events in RTX treated subjects.

TABLE 4

| Treatment Emergent-Adverse Events (TEAE) | Severity | Placebo All Cohorts (N = 10) | RTX All Cohorts (N = 57) |
|---|---|---|---|
| Procedural pain | Mild | 7 (70.0%) | 37 (64.9%) |
|  | Moderate | 0 | 15 (26.3%) |
| Nausea | Mild | 2 (20.0%) | 18 (31.6%) |
|  | Moderate | 0 | 2 (3.5%) |
| Vomiting | Mild | 0 | 8 (14.0%) |
|  | Moderate | 0 | 2 (3.5%) |
| Hypertension | Mild | 0 | 4 (7.0%) |
|  | Moderate | 0 | 4 (7.0%) |
| Arthralgia | Mild | 1 (10.0%) | 4 (7.0%) |
|  | Moderate | 0 | 1 (1.8%) |
| Hypoesthesia | Mild | 0 | 5 (8.8%) |
| Areflexia | Mild | 0 | 2 (3.5%) |
|  | Moderate | 0 | 2 (3.5%) |
| EOG QTc prolonged | Mild | 1 (10.0%) | 3 (5.3%) |
| Headache | Mild | 0 | 3 (5.3%) |

In terms of efficacy, reduction in patient reported WOMAC A1 and NPRS pain scores was observed at all dose levels.

Figure 2:
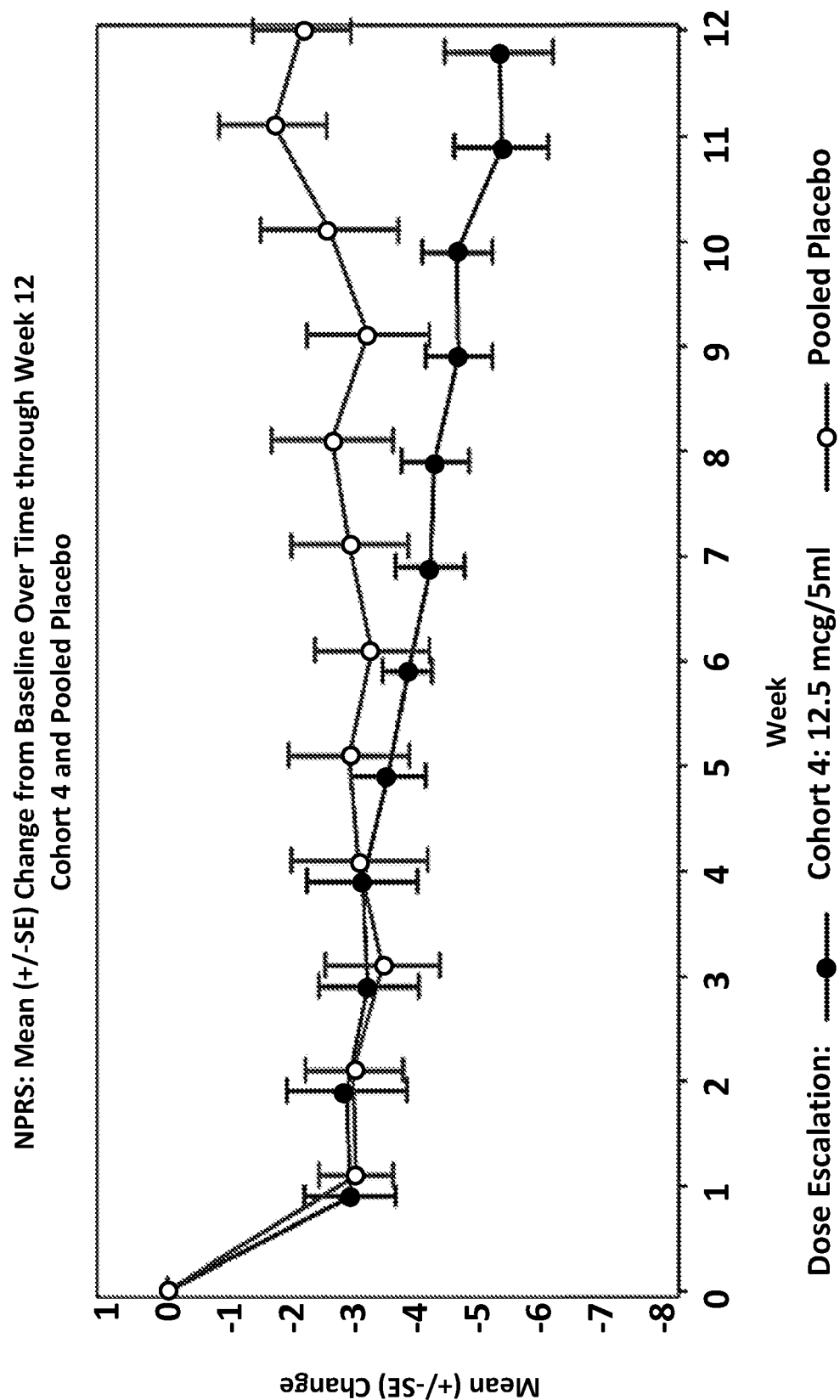
FIG. 2 shows the data from Example 3 demonstrating Numeric Pain Rating Scale (NPRS) score differences between RTX treated patients and placebo control patients.
Figure 3:
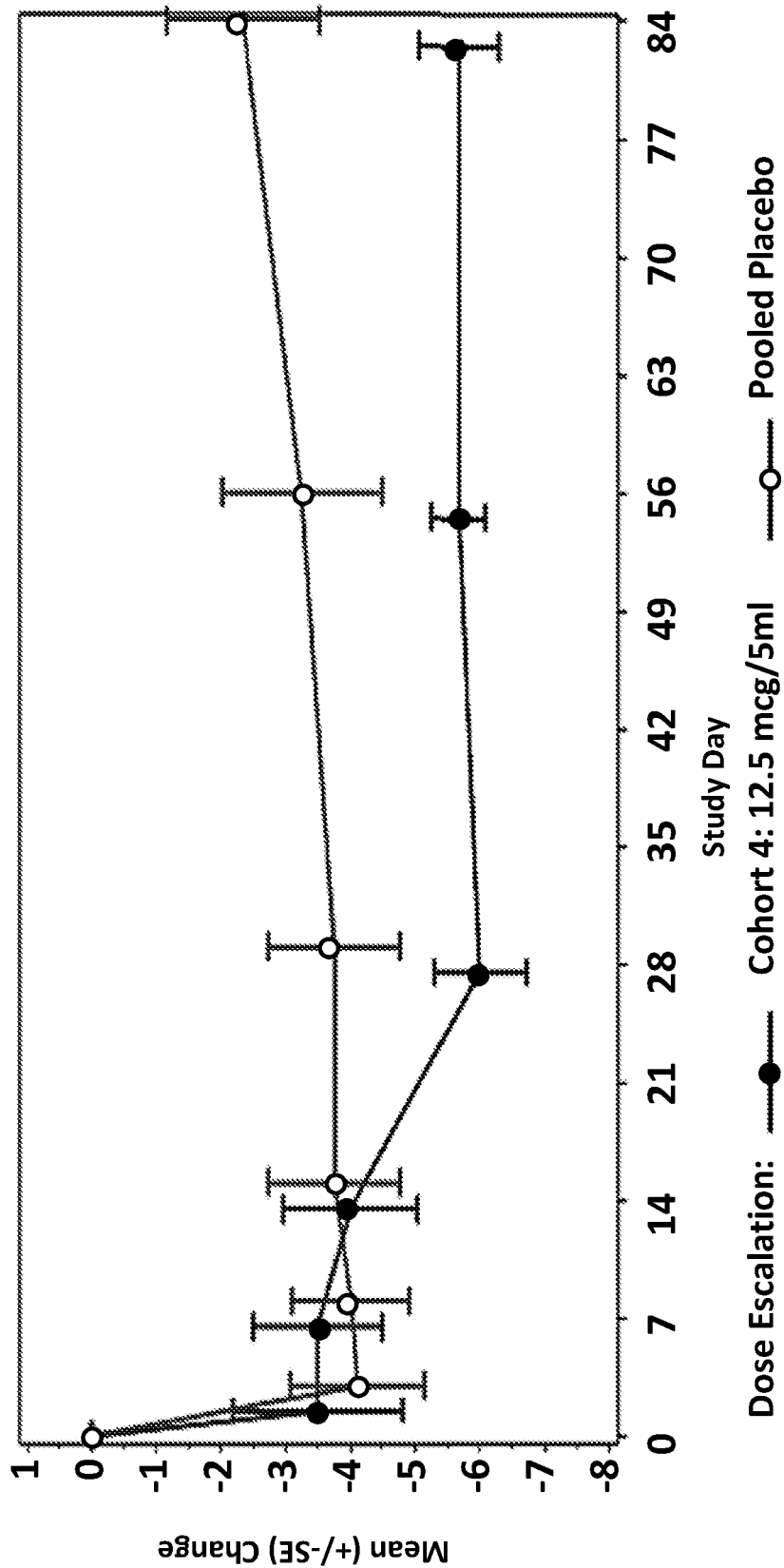
FIG. 3 shows the data from Example 3 demonstrating Western Ontario and McMaster Universities Osteoarthritis Index (WOMAC) score differences between RTX treated patients and placebo control patients.

As shown in FIG. 2, when analyzed as the change in the weekly average NPRS pain score from baseline to week 12, the mean change (standard deviation) in RTX treated patients of Cohort 4 with a dose/volume of 12.5 µg/5 ml was −5.30 (1.94) compared to a mean change in the pooled placebo patients of −2.14 (1.92). As shown in FIG. 3, when analyzed as the change in the weekly average WOMAC question A1 (pain on walking on flat surface) from baseline to week 12, the mean change (standard deviation) in RTX treated patients of Cohort 4 was −5.67 (1.51) compared to a mean change in the pooled placebo patients of −2.33 (2.88).

As summarized in Table 5 below, the pharmacokinetic data indicate that RTX is undetectable in most patients.

TABLE 5

| Cohort | Dose & Volume | Number of RTX subjects with PK measured | Number of subjects with BQL of RTX | Number of RTX subjects with quantifiable PK | $C_{max}$ | AUC (0-6 hr) (pg*hr/ml) |
|---|---|---|---|---|---|---|
| 1 | 5 µg/5 ml | 6 | 5 | 1 | 121 pg/ml at 1.08 hr | 509 |
| 4 | 12.5 µg/5 ml | 6 | 6 | 0 | N/A | N/A |
| 4a | 12.5 µg/10 ml | 6 | 5 | 1 | 103 pg/ml at 0.75 hr | 146 |
| 5 | 20 µg/5 ml | 6 | 4 | 2 | 71 pg/ml at 0.68 hr; 54 µg/ml at 0.8 hr | 68; 18.8 |
| 6 | 30 µg/5 or 10 ml | 6 | 5 | 1 | 87.8 pg/ml at 0.47 hr | 85.4 |

(BQL = below quantifiable limit)

What is claimed is:

1. A method for treating osteoarthritis (OA) pain comprising administering a therapeutically effective amount of resiniferatoxin (RTX) to a human subject in need thereof, wherein the administering is by an intra-articular injection to an affected joint; and wherein the composition is a pharmaceutical formulation comprising RTX and a pharmaceutically acceptable carrier at a concentration of 1 µg/mL to 50 µg/mL.

2. The method of claim 1, wherein the dose of RTX is from about 1 µg to about 100 µg.

3. The method of claim 2, wherein the dose of RTX is from about 5 µg to about 40 µg.

4. The method of claim 2, wherein the dose of RTX is about 12.5 µg.

5. The method of claim 2, wherein the dose of RTX is about 20 µg.

6. The method of claim 1, wherein the dose of RTX is about 5 µg, 12.5 µg, 20 µg or 30 µg, optionally wherein the dose is in a volume of about 2.5 ml to about 15 ml.

7. The method of claim 1, wherein the affected joint is a knee joint, a hip joint, a hand joint, a shoulder joint, an ankle joint, a foot joint, an elbow joint, a wrist joint, a sacroiliac joint, or a spine joint, or combinations thereof.

8. The method of claim 1, wherein the affected joint is a large joint.

9. The method of claim 1, wherein the RTX is administered to a single site.

10. The method of claim 1, wherein the RTX is administered to a plurality of sites.

11. The method of claim 1, wherein the pharmaceutically acceptable carrier comprises polysorbate 80, or wherein the pharmaceutically acceptable carrier comprises polyethylene glycol, or wherein the pharmaceutically acceptable carrier comprises a sugar or sugar alcohol or wherein the pharmaceutically acceptable carrier comprises a pharmaceutically acceptable buffer.

12. The method of claim 1, wherein the pharmaceutical formulation has a pH in the range of 6 to 7.6.

13. The method of claim 1, wherein the pharmaceutically acceptable carrier comprises a pharmaceutically acceptable salt.

14. The method of claim 1, wherein RTX is administered at least one time per year.

15. The method of claim 14, wherein the administration occurs within a time period of from about 1 week to about 12 months or more.

16. The method of claim 1, wherein the dose of RTX ranges from 0.1-1 µg, 1-2 µg, 2-5 µg, 5-10 µg, 10-20 µg, 20-30 µg, 30-40 µg, 40-50 µg, 50-60 µg, 60-70 µg, 70-80 µg, 80-90 µg, or 90-100 µg.

17. The method of claim 2, wherein the dose of RTX is from about 10 µg to about 30 µg.

18. The method of claim 2, wherein the dose of RTX is from about 15 µg to about 25 µg.

* * * * *